United States Patent [19]

Heider et al.

[11] Patent Number: 4,716,169

[45] Date of Patent: Dec. 29, 1987

[54] IMIDAZO[1,2A]PYRIDINES AND THEIR USE AS CARDIOTONIC AGENTS

[75] Inventors: Joachim Heider, Warthausen; Norbert Hauel; Volkhard Austel, both of Biberach; Klaus Noll, Warthausen; Andreas Bomhard, Biberach; Jacques van Meel, Biberach; Willi Diederen, Biberach, all of Fed. Rep. of Germany

[73] Assignee: Dr. Karl Thomae GmbH, Biberach an der Riss, Fed. Rep. of Germany

[21] Appl. No.: 810,008

[22] Filed: Dec. 17, 1985

[30] Foreign Application Priority Data

Dec. 21, 1984 [DE] Fed. Rep. of Germany ....... 3446778

[51] Int. Cl.$^4$ ..................... A61K 31/41; C07D 471/04
[52] U.S. Cl. .................................. 514/299; 514/243; 514/246; 514/248; 514/249; 546/121; 544/282; 544/235; 544/349
[58] Field of Search ......................... 546/121; 514/299

[56] References Cited

PUBLICATIONS

Hack's Chemical Dictionary p. 424, 4th ed.

Primary Examiner—Henry R. Jiles
Assistant Examiner—J. Richter
Attorney, Agent, or Firm—David E. Frankhouser; Alan R. Stempel; Mary-Ellen M. Timbers

[57] ABSTRACT

The invention relates to new imidazo derivatives of the formula

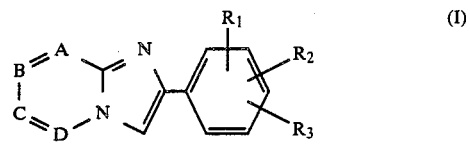

wherein "A-D and $R^1$-$R^3$ are as defined in the specification".

The new compounds have valuable pharmacological properties, particularly antithrombotic and cardiovascular properties such as a cardiotonic activity and/or an effect on blood pressure, and can be prepared using methods known per se.

8 Claims, No Drawings

IMIDAZO[1,2A]PYRIDINES AND THEIR USE AS CARDIOTONIC AGENTS

This invention relates to new imidazo derivatives of general formula

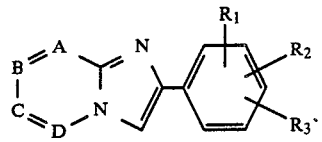

and the acid addition salts thereof, particularly the physiologically acceptable acid addition salts thereof with inorganic or organic acids which have valuable pharmacological properties, particularly antithrombotic and cardiovascular properties such as a cardiotonic effect and/or an effect on blood pressure.

In general formula I above none, one or two of the groups A, B, C or D represent nitrogen atoms, another of the groups A, B, C or D represents a methine group optionally substituted by a halogen atom or by an alkylmercapto, alkylsulphonyloxy, amino, alkylamino, dialkylamino or alkanoylamino group, another of the groups A, B, C or D represents a methine group optionally substituted by an alkylmercapto group; and, the other groups A, B, C or D represent methine groups;

$R_1$ and $R_2$ together with two carbon atoms of the phenyl ring between them form a phenyl ring optionally substituted by an alkoxy group and, when $R_1$ and $R_2$ do form such a phenyl ring, $R_3$ represents a hydrogen atom, a hydroxy, alkoxy or alkylsulphonyloxy group; or, $R_1$ represents a phenylalkoxy, alkylsulphonyloxy, alkylsulphonamido, N-alkyl-alkylsulphonamido, aminosulphonyl, alkylaminosulphonyl or dialkylaminosulphonyl group, or in the 4 position an alkanoylamino, aminocarbonyl, alkylaminocarbonyl or dialkylaminocarbonyl group, it being provided that if said compound of formula I is an imidazo[1,2-a]pyrimidine, an imidazo[1,2-b]pyridazine or an imidazo[2,1-f][1,2,4]triazine or, if one or two of the groups A, B, C or D represent one of the above-mentioned substituted methine groups, then $R_1$ may also represent an amino, hydroxy, methoxy or cyano group in the 4 position;

$R_2$ represents a hydrogen atom, a hydroxy or alkoxy group; and, $R_3$ represents a hydrogen atom or an alkoxy group;

wherein in all the above-mentioned groups the alkyl part may contain one or two carbon atoms.

Thus, the present invention relates particularly to the correspondingly substituted imidazo[1,2-a]-pyrimidines, imidazo[1,2-c]pyrimidines, imidazo[1,2-a][1,3,5]triazines, imidazo[2,1-f][1,2,4]triazines, imidazo[1,2-a]pyrazines, imidazo[1,2-d][1,2,4]triazines, imidazo[1,2-b][1,2,4]triazines, imidazo[1,2-b]pyridazines, imidazo[1,2-a]pyridines and imidazo[2,1-c][1,2,4]triazines of general formula I above and the acid addition salts thereof, particularly the physiologically acceptable acid addition salts thereof.

Thus, as examples of the definitions of the groups $R_1$ to $R_3$ mentioned hereinbefore:

$R_1$ and $R_2$ together with the phenyl ring may represent, in particular, a naphth-1-yl, naphth-2-yl, 2-methoxy-naphth-1-yl, 3-methoxy-naphth-1-yl, 4-methoxy-naphth-1-yl, 5-methoxy-naphth-1-yl, 6-methoxy-naphth-1-yl, 7-methoxy-naphth-1-yl, 8-methoxy-naphth-1-yl, 1-methoxy-naphth-2-yl, 3-methoxy-naphth-2-yl, 4-methoxy-naphth-2-yl, 5-methoxy-naphth-2-yl, 6-methoxy-naphth-2-yl, 7-methoxy-naphth-2-yl, 8-methoxy-naphth-2-yl, 2-hydroxy-naphth-1-yl, 3-hydroxy-naphth-1-yl, 4-hydroxy-naphth-1-yl, 6-hydroxy-naphth-1-yl, 2-methanesulphonyloxy-naphth-1-yl or 4-methanesulphonyloxy-naphth-1-yl group and, when $R_1$ and $R_2$ do form such a phenyl ring, $R_3$ may represent a hydrogen atom, a hydroxy, methoxy, ethoxy, methanesulphonyloxy or ethanesulphonyl group; or $R_1$ may represent a hydroxy, methoxy, ethoxy, benzyloxy, 1-phenylethoxy, 2-phenylethoxy, amino, acetamido, methylsulphonyloxy, ethylsulphonyloxy, aminosulphonyl, methylaminosulphonyl, ethylaminosulphonyl, dimethylaminosulphonyl, diethylaminosulphonyl, N-methyl-ethylaminosulphonyl, methylsulphonamido, ethylsulphonamido, N-methyl-methylsulphonamido, N-ethyl-methylsulphonamido, N-methylethylsulphonamido, N-ethyl-ethylsulphonamido, cyano, aminocarbonyl, methylaminocarbonyl, ethylaminocarbonyl, dimethylaminocarbonyl, diethylaminocarbonyl or N-methylethylaminocarbonyl group;

$R_2$ may represent a hydrogen atom, a hydroxy, methoxy or ethoxy group; and, $R_3$ may represent a hydrogen atom, a methoxy or ethoxy group.

Preferred compounds of general formula I above are those wherein 0, 1 or 2 of the groups A, B, C or D represent nitrogen atoms;

another of the groups A, B, C or D represents a methine group optionally substituted by a chlorine or bromine atom or by a methylmercapto, methylsulphonyloxy, amino, methylamino, dimethylamino or acetamido group;

another of the groups A, B, C or D represents a methine group optionally substituted by a methylmercapto group; and, the other groups A, B, C or D represent methine groups, $R_1$ and $R_2$ together with two carbon atoms of the phenyl ring between them represent a phenyl ring optionally substituted by a methoxy group and, when $R_1$ and $R_2$ do form such a phenyl group, $R_3$ represents a hydrogen atom, a hydroxy, methoxy or methanesulphonyloxy group; or, $R_1$ represents an acetamido, methylsulphonyloxy, methylsulphonamido, N-methyl-methylsulphonamido, aminosulphonyl, methylaminosulphonyl, dimethylaminosulphonyl, aminocarbonyl, methylaminocarbonyl or dimethylaminocarbonyl group;

$R_2$ represents a hydrogen atom or a hydroxy or methoxy group; and, $R_3$ represents a hydrogen atom or a methoxy group.

Particularly preferred are those compounds wherein $R_1$ is in the 2 or 4 position and $R_2$ is in the remaining 2 or 4 position.

However, the most preferred compounds of general formula I above are those wherein 0, 1 or 2 of the groups A, B, C or D represent nitrogen atoms and the other groups A, B, C or D represent methine groups;

$R_1$, in the 2 or 4 position represents a methylsulphonyloxy, methylsulphonamido, N-methyl-methylsulphonamido, aminosulphonyl, methylaminosulphonyl or dimethylaminosulphonyl group;

$R_2$, in the remaining 2 or 4 position, represents a methoxy group; and, $R_3$ represents a hydrogen atom.

According to the invention, the new compounds are obtained by the following processes:

(a) Reacting a compound of general formula:

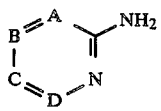 (II)

wherein

A, B, C and D are as hereinbefore defined, with a compound of general formula

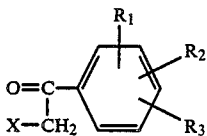 (III)

wherein $R_1$, $R_2$ and $R_3$ are as hereinbefore defined and

X represents a nucleophilically exchangeable group such as a halogen atom, e.g. a chlorine or bromine atom.

The reaction is conveniently carried out in a solvent or mixture of solvents such as ethanol, isopropanol, benzene, glycol, glycolmonomethylether, dimethylformamide or dioxan, for example at temperatures of between 0° and 150° C., preferably at temperatures of between 20° and 100° C. However, the reaction may also be carried out without a solvent.

(b) In order to prepare compounds of general formula I wherein $R_1$ represents an alkylsulphonyloxy, alkylsulphonamido or N-alkyl-alkylsulphonamido group:

Reaction of a compound of general formula:

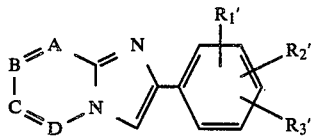 (IV)

wherein

A, B, C and D are as hereinbefore defined and the groups $R_1'$, $R_2'$ and $R_3'$ have the meanings given for $R_1$, $R_2$ or $R_3$, with the exception of the alkylsulphonyloxy, alkylsulphonamido and N-alkyl-alkylsulphonamido group, but one of the groups $R_1'$, $R_2'$ or $R_3'$ must represent a hydroxy, amino, methylamino or ethylamino group, with a compound of general formula $$R_4-SO_2-Y \qquad (V)$$

wherein $R_4$ represents a methyl or ethyl group and

Y represents a nucleophilically exchangeable group such as a halogen atom or an alkoxy group, e.g. a chlorine or bromine atom or a methoxy, ethoxy or benzyloxy group.

The reaction is conveniently carried out in a solvent or mixture of solvents such as water, methanol, ethanol, isopropanol, methylene chloride, ether, tetrahydrofuran, dioxan, dimethylformamide or benzene, optionally in the presence of an acid binding agent such as sodium carbonate, triethylamine or pyridine, while the latter two may simultaneously also be used as solvent, preferably at temperatures of between 0° and 100° C., e.g. at temperatures of between ambient temperature and 50° C.

(c) In order to prepare compounds of general formula I wherein at least one of the groups $R_1$, $R_2$ or $R_3$ represents an alkoxy group or $R_1$ represents an N-alkyl-alkylsulphonamido group:

Alkylation of a compound of general formula:

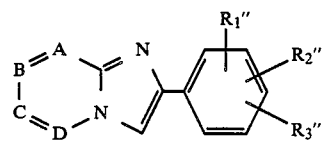 (VI)

wherein

A, B, C and D are as hereinbefore defined and $R_1''$, $R_2''$ and $R_3''$ have the meanings given for $R_1$, $R_2$ or $R_3$ hereinbefore, but at least one of the groups $R_1''$, $R_2''$ or $R_3''$ must represent a hydroxy and/or an alkylsulphonamido group, with a compound of general formula $$R_4-Z \qquad (VII)$$

wherein $R_4$ represents a methyl or ethyl group and

Z represents a nucleophilically exchangeable group such as a halogen atom or a sulphonyloxy group e.g. a chlorine, bromine or iodine atom or a methylsulphonyloxy, methoxysulphonyloxy or p-toluenesulphonyloxy group.

The reaction is carried out with an alkylating agent such as methyliodide, ethyliodide, dimethylsulphate or methyl p-toluenesulphonate, conveniently in a solvent such as tetrahydrofuran, dioxan, dimethylformamide, sulfolan, dimethylsulphoxide or ethylene glycoldimethylether, optionally in the presence of an acid-binding agent such as potassium carbonate, potassium tert-.butoxide, triethylamine or pyridine, while the latter two may simultaneously also be used as solvent, at temperatures of between 0° and 100° C., preferably at temperatures of between 20° and 50° C.

(d) In order to prepare compounds of general formula I wherein $R_1$ represents an aminosulphonyl, alkylaminosulphonyl or dialkylaminosulphonyl group:

Reaction of a compound of general formula:

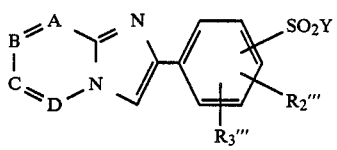 (VIII)

wherein

A, B, C and D are as hereinbefore defined, $R_2'''$ and $R_3'''$ have the meanings given for $R_1$, $R_2$ and $R_3$ hereinbefore, with the exception of the aminosulphonyl, alkylaminosulphonyl or dialkylaminosulphonyl group and Y represents a nucleophilically exchangeable group such as a halogen atom or an alkoxy group, e.g. a chlorine atom or a methoxy or ethoxy group, with an amine of general formula

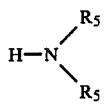
(IX)

wherein

R$_5$ represents a hydrogen atom or a methyl or ethyl group.

The reaction is conveniently carried out in a solvent or mixture of solvents such as water, methanol, ethanol, isopropanol, methylene chloride, ether, tetrahydrofuran, dioxan, dimethylformamide or benzene, optionally in the presence of an acid binding agent such as sodium carbonate, triethylamine or pyridine, while the latter two may simultaneously also be used as solvent, preferably at temperatures of between 0° and 100° C., e.g. at temperatures of between ambient temperature and 50° C.

(e) In order to prepare compounds of general formula I wherein at least one of the groups R$_1$, R$_2$ or R$_3$ represents or contains an amino, hydroxy or aminocarbonyl group:

Hydrolysis of a compound of general formula:

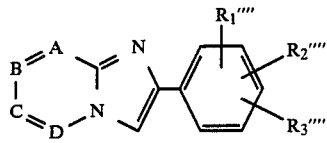
(X)

wherein

A, B, C and D have the meanings given for A, B, C and D hereinbefore, with the exception of the methine group substituted by a halogen atom or by an alkylmercapto, alkylsulphonyloxy or phenylalkoxy group, R$_1''''$ to R$_3''''$ have the meanings given for R$_1$ to R$_3$ hereinbefore, but one of the groups R$_1''''$, R$_2''''$ or R$_3''''$ must contain or represent a cyano, alkoxy, alkanoylamino or alkylsulphonyloxy group.

The reaction is conveniently carried out either in the presence of an acid such as hydrochloric, sulphuric, phosphoric or trichloroacetic acid or in the presence of a base such as sodium hydroxide or potassium hydroxide or the alkali metal salt of a corresponding alcohol in a melt or in a suitable solvent such as water, water/methanol, ethanol, water/ethanol, water/isopropanol or water/dioxan at temperatures of between −10° and 120° C., e.g. at temperatures of between ambient temperature and the boiling temperature of the reaction mixture.

However, the ether splitting is preferably carried out with boron tribromide in a solvent such as methylene chloride at temperatures of between −40° C. and ambient temperature.

The partial hydrolysis of the cyano group is, however, preferably carried out with concentrated sulphuric acid or with an alkali metal hydroxide solution in the presence of hydrogen peroxide, e.g. with sodium hydroxide solution/hydrogen peroxide, conveniently at ambient temperature.

(f) In order to prepare compounds of general formula I wherein at least two of the groups A, B, C or D represent methine groups or at least one of the groups R$_1$, R$_2$ or R$_3$ must represent a hydrogen atom:

Reductively splitting off one or two groups from a compound of general formula:

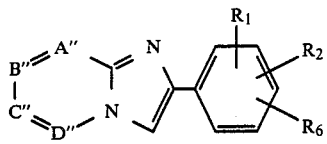
(XI)

wherein

R$_1$ and R$_2$ are as hereinbefore defined,

R$_6$ has the meanings given for R$_3$ hereinbefore and A'', B'', C'' and D'' have the meanings given for A, B, C and D hereinbefore, but at least one of the groups R$_6$, A'', B'', C'' or D'' must represent or contain a reductively cleavable group, e.g. a chlorine, bromine or iodine atom or an alkylmercapto group.

The reductive cleaving is preferably effected by hydrogenolysis. This is preferably carried out in a solvent such as methanol, ethanol, isopropanol, glacial acetic acid, ethyl acetate, dimethylformamide or water, optionally in the presence of an inorganic acid such as hydrochloric or hydrobromic acid at temperatures of between −10° C. and 100° C., preferably at 0° C. to 60° C. in the presence of a catalyst such as Raney nickel, platinum, platinum oxide or palladium on charcoal. Any benzyloxy groups present is converted into a hydroxy group during the reaction.

If according to the invention a compound of general formula I is obtained wherein one of the groups A, B, C or D represents a methine group substituted by a halogen atom, this may be converted by aminolysis into the corresponding amino compound of general formula I.

The subsequent aminolysis is conveniently carried out in a solvent or mixture of solvents such as water, methanol, ethanol, isopropanol, methylene chloride, ether, tetrahydrofuran, dioxan, dimethyl formamide or benzene, optionally in the presence of an acid-binding agent such as sodium carbonate, triethylamine or pyridine, while the latter two may simultaneously also be used as solvent, preferably at temperatures of between 0° and 100° C., e.g. at temperatures of between ambient temperature and 50° C.

The compounds of general formula I obtained according to the invention may, if desired, be converted into the physiologically acceptable acid addition salts thereof with inorganic or organic acids. Examples of suitable acids include hydrochloric, hydrobromic, sulphuric, phosphoric, fumaric, succinic, tartaric, citric, lactic, maleic and methanesulphonic acid.

The compounds of general formulae II to XI used as starting materials are known from the literature in some cases or may be obtained by methods known from the literature.

Thus, for example, the compounds of general formulae IV, VI, VIII, X and XI used as starting materials are obtained by reacting a corresponding amino compound with a corresponding α-bromo-acetophenone optionally followed by chlorosulphonation.

As already mentioned hereinbefore, the new compounds of general formula I and the physiologically acceptable acid addition salts thereof have superior pharmacological properties, particularly antithrombotic and cardiovascular properties such as a cardiotonic activity and/or an effect on blood pressure.

For example, the following compounds:

A=2-(4-Methoxy-2-methylsulphonamide-phenyl)-imidazo[1,2-a]pyrimidine,
B=2-(2-Methoxy-4-methylsulphonyloxy-phenyl)-imidazo]1,2-a]pyrimidine,
C=2-(2-Methoxy-4-methylsulphonyloxy-phenyl)-imidazo[1,2-a]pyrazine,
D=2-(2-Methoxy-4-methylsulphonyloxy-phenyl)-imidazo[1,2-b]pyridazine,
E=2-(2-Methoxy-4-methylsulphonamide-phenyl)-imidazo[1,2-a]pyridine and
F=2-(2-Methoxy-4-aminosulphonyl-phenyl)-imidazo[1,2-a]pyrimidine were tested for their biological properties as follows:

Determining the positive inotropic effect on pithed guinea pigs

The tests were carried out on pithed guinea pigs. The animals were respirated with 50% $O_2$+50% $N_2$. The arterial blood pressure was measured in the right carotid artery using a Bell and Howell pressure transducer (4-327-I). To determine the positive inotropic effect, the pressure in the left ventricle (LV) was measured with a catheter-tip manometer (Millar PR-249). The LV-dp/dtmax was obtained using a differentiator. The substances being tested were injected into a jugular vein. 0.9% NaCl+polydiol 200 (1:1) was used as solvent.

Each substance was tested on 3 guinea pigs. The doses were 0.1–3 mg/kg i.v. The following Table contains the average values at 1 mg/kg i.v.

| Substance | Dosage mg/kg i.v. | Increase in LV-dp/dtmax |
|---|---|---|
| A | 1 | 77% |
| B | 1 | 74% |
| C | 1 | 100% |
| D | 1 | 56% |
| E | 1 | 76% |
| F | 1 | 56% |

The new compounds are well tolerated; when substances A to F were tested up to a dosage of 3 mg/kg i.v. no toxic effects on the heart or circulatory damage of any kind could be detected.

In view of their biological properties, the compounds of general formula I prepared according to the invention and the physiologically acceptable acid addition salts thereof are suitable for treating cardiac insufficiency of various origins since they increase the contractile force of the heart and partly by reducing blood pressure they facilitate the emptying of the heart.

For this purpose, the new compounds and the physiologically acceptable acid addition salts thereof, optionally together with other active substances, may be incorporated in conventional pharmaceutical preparations such as plain or coated tablets, powders, suppositories, suspensions, ampoules or drops. The single dosage is from 0.1–15 mg/kg of body weight, preferably from 3–10 mg/kg of body weight, 1–4 times a day.

The Examples which follow are intended to illustrate the invention:

EXAMPLE 1

6-Chloro-2-(4-methoxy-2-methylsulphonamido-phenyl)-imidazo[1,2-b]pyridazine 3.2 g (0.01 mol) of α-Bromo-4-methoxy-2-methylsulphonamido-acetophenone and 2.6 g (0.02 mol) of 3-amino-6-chloro-pyridazine are dissolved in 30 ml of dimethylformamide, stirred for 16 hours at ambient temperature and then poured onto 100 ml of water. The product precipitated is suction filtered, washed with water and dried in vacuo at 90° C. The crude product is purified by chromatography on silica gel (0.032–0.063 mm), eluant: methylene chloride.

Yield: 62.3% of theory, M.p.: 208°–209° C.: Calculated: C 47.66 H 3.11 N 15.88 Cl 10.05 S 9.25: Found: 47.67 3.37 16.08 10.27 9.20.

EXAMPLE 2

2-(2-Methoxy-4-methylsulphonyloxy-phenyl)-6-methylsulphonyloxy-imidazo[1,2-b]pyridazine 0.3 g (1.17 mmol) of 2-(2-Methoxy-4-hydroxy-phenyl)-5H-imidazo[1,2-b]pyridazin-6-one are dissolved in 10 ml of 1N sodium hydroxide solution. At 20° C., 1.3 g (1.17 mmol) of methanesulphonic acid chloride is added dropwise. By simultaneously adding 2N sodium hydroxide solution the pH is kept at 10–11.

Then the mixture is stirred for a further 3.5 hours at 20° C., stirred with ice water, suction filtered and dried. It is purified by heating with 20 ml of ethanolic hydrochloric acid and subsequently triturating with acetone and ether.

Yield: 49.5% of theory, M.p.: 243°–248° C. (decomp.) Mass spectrum: $M^+$: 413 m/e.

EXAMPLE 3

2-[4-Hydroxy-2-(N-methyl-methylsulphonamido)-phenyl]-imidazo[1,2-a]pyridine 1.1 g (3.6 mmol) of 2-(4-Hydroxy-2-methylsulphonamido-phenyl)-imidazo[1,2-a]pyridine are dissolved in 10 ml of dimethylsulphoxide, then 0.6 g (4.3 mmol) of potassium carbonate and 1.1 ml (18 mmol) of methyliodide are added. The mixture is stirred at ambient temperature for one hour. It is poured onto about 100 ml of ice water and the precipitate is suction filtered. It is then washed with water.

Yield: 95.6% of theory, M.p.: 177°–180° C. Calculated: C 56.76 H 4.76 N 13.24 S 10.10: Found: 55.02 4.69 12.82 10.09.

EXAMPLE 4

2-(4-Hydroxy-2-methylsulphonamido-phenyl)-imidazo[1,2-a]pyrimidine

Prepared from 2-amino-pyrimidine and α-bromo-4-hydroxy-2-methylsulphonamido-acetophenone analogously to Example 1.

Yield: 17.6% of theory, M.p.: 264°–266° C. Calculated: C 51.29 H 3.97 N 18.40 S 10.53: Found: 51.16 4.24 18.48 10.49.

EXMAPLE 5

2-(4-Hydroxy-2-methylsulphonamido-phenyl)-imidazo[1,2-a]pyridine

Prepared from 2-amino-pyridine and α-bromo-4-hydroxy-2-methylsulphonamido-acetophenone analogously to Example 1.

Yield: 13.3% of theory, M.p.: 250°–253° C. Calculated: C 55.44 H 4.32 N 13.85 S 10.57: Found: 55.16 4.56 13.67 10.70.

EXAMPLE 6

2-(4-Methoxy-2-methylsulphonamido-phenyl)-imidazo[1,2-a]pyrimidine

Prepared from 2-amino-pyrimidine and α-bromo-2-methylsulphonamido-4-methoxy-acetophenone analogously to Example 1.

Yield: 46.9% of theory, M.p.: 252°–254° C. Calculated: C 52.81 H 4.43 N 17.59 S 10.07: Found: 52.64 4.21 17.77 10.02.

EXAMPLE 7

2-(2-Hydroxy-4-methylsulphonyloxy-phenyl)-imidazo[1,2-a]pyrimidine

Prepared from 2-amino-pyrimidine and α-bromo-2-hydroxy-4-methylsulphonyloxy-acetophenone analogously to Example 1.

Yield: 32.7% of theory, M.p.: 244°–246° C. Calculated: C 51.14 H 3.63 N 13.76 S 10.50: Found: 51.08 3.69 13.52 10.55.

EXAMPLE 8

2-(2-Methoxy-4-methylsulphonyloxy-phenyl)-imidazo[1,2-a]pyrimidine

Prepared from 2-amino-pyrimidine and α-bromo-2-methoxy-4-methylsulphonyloxy-acetophenone analogously to Example 1.

Yield: 6.2% of theory, M.p.: 182°–184° C. Calculated: C 52.66 H 4.10 N 13.16 S 10.04: Found: 52.40 3.99 13.00 10.11.

EXAMPLE 9

2-(2-Methoxy-4-methylsulphonyloxy-phenyl)-imidazo[1,2-a]pyridine

Prepared from 2-amino-pyridine and α-bromo-2-methoxy-4-methylsulphonyloxy-acetophenone analogously to Example 1.

Yield: 65.5% of theory, M.p.: 143°–146° C. Calculated: C 56.58 H 4.43 N 8.79 S 10.07: Found: 56.84 4.23 8.76 10.02.

EXAMPLE 10

2-(4-Methoxy-2-methylsulphonamido-phenyl)-imidazo[1,2-a]pyridine

Prepared from 2-amino-pyridine and α-bromo-4-methoxy-2-methylsulphonylamido-acetophenone analogously to Example 1.

Yield: 6.2% of theory, M.p.: 248°–251° C. Analysis of the hydrochloride: Calculated: C 50.85 H 4.55 N 11.86 Cl 10.01 S 9.05: Found: 51.11 4.34 11.55 9.97 9.01.

EXAMPLE 11

2-(4-Dimethylaminosulphonyl-phenyl)-imidazo[1,2-a]pyrimidine

Prepared from 2-amino-pyrimidine and α-bromo-4-dimethylaminosulphonyl-acetophenone analogously to Example 1.

Yield: 45.6% of theory, M.p.: 280°–283° C. Calculated: C 55.61 H 4.67 N 18.53 S 10.61: Found: 55.41 4.81 18.18 10.88.

EXAMPLE 12

2-(4-Cyano-phenyl)-imidazo[1,2-a]pyrimidine

Prepared from 2-amino-pyrimidine and α-bromo-4-cyano-acetophenone analogously to Example 1.

Yield: 56.8% of theory, M.p.: 335°–336° C. Calculated: C 70.90 H 3.66 N 25.44: Found: 70.99 3.70 25.54.

EXAMPLE 13

2-(4-Methylsulphonamido-phenyl)-imidazo[1,2-a]pyrimidine

Prepared from 2-amino-pyrimidine and α-bromo-4-methylsulphonamido-acetophenone analogously to Example 1.

Yield: 22.6% of theory, M.p.: 260°–266° C. Calculated: C 54.15 H 4.20 N 19.43 S 11.12: Found: 53.82 4.27 19.66 11.07.

EXAMPLE 14

2-(4-Methylsulphonyloxy-phenyl)-imidazo[1,2-a]pyrimidine

Prepared from 2-amino-pyrimidine and α-bromo-4-methylsulphonyloxy-acetophenone analogously to Example 1.

Yield: 22.4% of theory, M.p.: 238°–240° C. Calculated: C 53.97 H 3.83 N 14.53 S 11.08: Found: 53.77 3.71 14.65 10.82.

EXAMPLE 15

2-(4-Methoxy-phenyl)-imidazo[1,2-a]pyrimidine

Prepared from 2-amino-pyrimidine and α-bromo-4-methoxy-acetophenone analogously to Example 1.

Yield: 42.2% of theory, M.p.: 198°–200° C. Calculated: C 69.32 H 4.92 N 18.66: Found: 69.10 4.81 18.80.

EXAMPLE 16

7-(4-Methylsulphonyloxy-2-methoxy-phenyl)-imidazo[2,1-c][1,2,4]triazine

Prepared from 3-amino[1,2,4]triazine and α-bromo-4-methylsulphonyloxy-2-methoxy-acetophenone analogously to Example 1.

Yield: 64% of theory, M.p.: 194°–196° C. Calculated: C 48.74 H 3.78 S 10.01: Found: 48.66 3.67 9.98.

EXAMPLE 17

7-(4-Methylsulphonyloxy-2-methoxy-phenyl)-imidazo[1,2-a][1,3,5]triazine

Prepared from 2-amino[1,3,5]triazine and α-bromo-4-methylsulphonyloxy-2-methoxy-acetophenone analogously to Example 1.

Yield: 8.5% of theory, $R_f$ value of the amorphous product: 0.18 (Merck silica gel, eluant: $CH_2Cl_2/C_2H_5OH$ (10:1)): Mass spectrum: $M^+ = 320$ m/e.

EXAMPLE 18

2-(4-Methylsulphonyloxy-2-methoxy-phenyl)-imidazo[1,2-a]pyrazine

Prepared from 2-amino-pyrazine and α-bromo-4-methylsulphonyloxy-2-methoxy-acetophenone analogously to Example 1.

Yield: 3.4% of theory, M.p.: 185°–187° C. Calculated: C 52.60 H 4.10 N 13.16: Found: 52.40 3.87 12.97.

EXAMPLE 19

2-(4Methoxy-2-methylsulphonamido-phenyl)-imidazo[1,2-b]pyridazine

Prepared from 3-amino-pyridazine-hydrochloride and α-bromo-4-methoxy-2-methylsulphonamido-acetophenone analogously to Example 1.

Yield: 10% of theory, M.p.: 198°–200° C. Calculated: C 52.81 H 4.43 N 17.60 S 10.07: Found: 53.08 4.28 17.69 10.73.

EXAMPLE 20

2-(2-Methoxy-4-methylsulphonyloxy-phenyl)-imidazo[1,2-b]pyridazine

Prepared from 3-amino-pyridazine-hydrochloride and α-bromo-2-methoxy-4-methylsulphonyloxy-acetophenone analogously to Example 1.

Yield: 7% of theory, M.p.: 150°–151° C. Calculated: C 52.65 H 4.10 N 13.16 S 10.04: Found: 52.88 4.29 13.28 9.94.

EXAMPLE 21

6-Chloro-2-(2-methoxy-4-methylsulphonyloxy-phenyl)-imidazo[1,2-b]pyridazine

Prepared from 3-amino-6-chloro-pyridazine and α-bromo-2-methoxy-4-methylsulphonyloxy-acetophenone analogously to Example 1.

Yield: 31.1% of theory, M.p.: 182°–183° C. Calculated: C 47.53 H 3.42 N 11.88 Cl 10.02 S 9.06: Found: 47.51 3.30 11.58 9.86 8.92.

EXAMPLE 22

2-(4-Acetamido-phenyl)-6-chloro-imidazo[1,2-b]pyridazine

Prepared from 3-amino-6-chloro-pyridazine and α-bromo-4-acetophenone analogously to Example 1.

Yield: 73.3% of theory, M.p.: 308°–312° C. Calculated: C 58.65 H 3.87 N 19.54 Cl 12.37: Found: 58.92 3.98 19.70 12.19.

EXAMPLE 23

6-(4-Methoxy-phenyl)-2,4-bis(methylmercapto)-imidazo[2,1-f][1,2,4]triazine

Prepared from 6-amino-3,5-bis(methylmercapto)-[1,2,4]triazine and α-bromo-4-methoxy-acetophenone in dimethylformamide analogously to Example 1.

Yield: 71.25% of theory, M.p.: 167°–169° C. Calculated: C 52.83 H 4.43 N 17.60 S 20.19: Found: 52.58 4.50 17.43 20.06.

EXAMPLE 24

6-(4-Hydroxy-2-methoxy-phenyl)-2,4-bis(methylmercapto)-imidazo[2,1-f][1,2,4]triazine Prepared from 6-amino-3,5-bis(methylmercapto)-[1,2,4]triazine and α-chloro-2-methoxy-4-hydroxy-acetophenone analogously to Example 1.

Yield: 46.4% of theory, M.p.: 189°–191° C. Calculated: C 50.30 H 4.22 N 16.76 S 19.18: Found: 50.10 4.11 16.78 19.18.

EXAMPLE 25

2-(4-Dimethylaminosulphonyl-phenyl)-imidazo[1,2-a]pyrimidine 2.9 g (0.01 mol) of 2-(4-Chlorosulphonyl-phenyl)-imidazo[1,2-a]pyrimidine are suspended in 60 ml of a 40% solution of dimethylamine in water. The mixture is heated to 50° C. for 30 minutes, diluted with 50 ml of water, extracted with ethyl acetate, then the ethyl acetate extract is dried and evaporated to dryness. The residue is recrystallised from dimethylformamide.

Yield: 68.5% of theory, M.p.: 280°–283° C. Calculated: C 55.61 H 4.67 N 18.53 S 10.61: Found: 55.41 4.81 18.28 10.88.

EXAMPLE 26

2-(2-Methoxy-4-methylsulphonamido-phenyl)-imidazo[1,2-a]pyrimidine

Prepared from 2-amino-pyrimidine and α-bromo-2-methoxy-4-methylsulphonamido-acetophenone analogously to Example 1.

Yield: 58% of theory, M.p.: 264°–266° C. Calculated: C 52.81 H 4.43 N 17.59 S 10.07: Found: 52.60 4.47 17.39 10.10.

EXAMPLE 27

2-(2-Methoxy-4-methylsulphonamido-phenyl)-imidazo[1,2-a]pyridine

Prepared from 2-amino-pyridine and α-bromo-2-methoxy-4-methylsulphonamido-acetophenone analogously to Example 1.

Yield: 84.8% of theory, M.p.: 235°–237° C. Calculated: C 56.76 H 4.76 N 13.24 S 10.10: Found: 56.56 4.90 13.17 10.02.

EXAMPLE 28

6-Chloro-2-(4-acetamido-2-methoxy-phenyl)-imidazo[1,2-b]pyridazine

Prepared from 3-amino-6-chloro-pyridazine and α-bromo-4-acetamido-2-methoxy-acetophenone analogously to Example 1.

Yield: 73% of theory, M.p.: 267°–269° C. (decomposition) Calculated: C 56.88 H 4.14 N 17.69 Cl 11.19: Found: 56.90 4.38 17.62 11.25.

EXAMPLE 29

2-(4-Methylsulphonamido-phenyl)-imidazo[1,2-b]pyridazine

Prepared from 2-(4-amino-phenyl)-imidazo[1,2-b]pyridazine methanesulphonic acid chloride in pyridine analogously to Example 2.

Yield: 94% of theory, M.p.: 240°–245° C. (decomposition) Calculated: C 54.16 H 4.20 N 19.44 S 11.12: Found: 53.70 4.14 19.64 11.28.

EXAMPLE 30

6-Chloro-(4-amino-phenyl)-imidazo[1,2-b]pyridazine

Prepared from 6-chloro-3-amino-pyridazine and α-bromo-4-amino-acetophenone analogously to Example 1.

Yield: 20% of theory, M.p.: 220°–228° C. NMR spectrum (dimethylsulphoxide): aromatic H: 6.6 and 7.7 ppm (2d, 4H) H in the 3 position: 8.6 ppm (s, 1H) H in the 8 and 9 position: 7.2 and 8.1 ppm (2d, 2H) UV spectrum (ethanol): 223 nm (0.47), 265 nm (0.31) 385 nm (0.25).

EXAMPLE 31

2-(4-Acetamido-phenyl)-imidazo[1,2-b]pyridazine

Prepared from 3-amino-pyridazine and α-bromo-4-acetamido-acetophenone analogously to Example 1.

Yield: 72% of theory, M.p.: 300°–305° C. (decomposition) $C_{14}H_{12}N_4O \times 0.75H_2O$ Calculated: C 63.26 H 5.12 N 21.08: Found: 63.37 4.87 21.26.

EXAMPLE 32

2-(4-Amino-phenyl)-imidazo[1,2-b]pyridazine

Prepared from 3-amino-pyridazine and α-bromo-4-aminoacetopheone analogously to Example 1.

Yield: 69% of theory, M.p.: 195°–202° C. Calculated: C 68.57 H 4.80 N 26.67: Found: 68.57 4.70 26.52.

EXAMPLE 33

2-(2,4-Dimethoxy-5-dimethylaminosulphonyl-phenyl)-imidazo[1,2-a]pyrimidine

Prepared from 2-(2,4-dimethoxy-5-chlorosulphonyl-phenyl)-imidazo[1,2-a]pyrimidine (prepared from 2-(2,4-dimethoxyphenyl[1,2-a]pyrimidine and chlorosulphonic acid) and 40% dimethylamine analogously to Example 25.

Yield: 42% of theory, M.p.: 246°–248° C. Calculated: C 50.51 H 5.28 N 14.72 S 8.85: Found: 50.30 5.28 14.74 8.86.

EXAMPLE 34

2-(2-Methoxy-4-aminocarbonyl-phenyl)-imidazo[1,2-a]pyrimidine

Prepared from 2-amino-pyrimidine and α-bromo-2-methoxy-4-aminocarbonyl-acetophenone analogously to Example 1.

Yield: 96.2% of theory, M.p.: 290°–291° C. Calculated: C 58.74 H 4.93 N 19.57: Found: 58.60 4.74 19.36.

EXAMPLE 35

2-(2-Methoxy-4-aminocarbonyl-phenyl)-imidazo[1,2-a]pyridine

Prepared from 2-amino-pyridine and α-bromo-2-methoxy-4-aminocarbonyl-acetophenone analogously to Example 1.

Yield: 56.6% of theory, M.p.: 263°–266° C. Calculated: C 67.41 H 4.90 N 15.72: Found: 67.14 4.97 15.53.

EXAMPLE 36

2-(2-Methoxy-4-aminosulphonyl-phenyl)-imidazo[1,2-a]pyrimidine

Prepared from 2-amino-pyrimidine and α-bromo-2-methoxy-4-aminosulphonyl-acetophenone analogously to Example 1.

Yield: 51.6% of theory, M.p.: 294°–296° C. Calculated: C 51.31 H 3.97 N 18.41 S 10.53: Found: 50.99 3.98 18.36 10.37.

EXAMPLE 37

2-(2-Methoxy-4-methylaminosulphonyl-phenyl)-imidazo[1,2-a]pyrimidine

Prepared from 2-amino-pyrimidine and α-bromo-2-methoxy-4-methylaminosulphonyl-acetophenone analogously to Example 1.

Yield: 41.2% of theory, M.p.: 304°–306° C. Calculated: C 52.81 H 4.43 N 17.59 S 10.07: Found: 52.55 4.36 17.63 9.91.

EXAMPLE 38

2-(2-Methoxy-4-methylaminosulphonyl-phenyl)-imidazo[1,2-a]pyridine

Prepared from 2-amino-pyridine and α-bromo-2-methoxy-4-methylaminosulphonyl-acetophenone analogously to Example 1.

Yield: 44.4% of theory, M.p.: 241°–244° C. Calculated: C 56.78 H 4.76 N 13.24 S 10.10: Found: 56.86 4.84 13.09 10.11.

EXAMPLE 39

2-(2-Methoxy-4-cyano-phenyl)-imidazo[1,2-a]pyrimidine

Prepared from 2-amino-pyrimidine and α-bromo-2-methoxy-4-cyano-acetophenone analogously to Example 1.

Yield: 56% of theory, M.p.: 289°–291° C. Calculated: C 67.19 H 4.03 N 22.39: Found: 67.00 3.99 22.46.

EXAMPLE 40

2-(3-Dimethylaminosulphonyl-4-methoxy-phenyl)-imidazo[1,2-a]pyrimidine-hydrobromide Prepared from 2-(4-methoxy-3-chlorosulphonyl-phenyl)-imidazo[1,2-a]pyrimidine (prepared from 2-(4-methoxy-phenyl)-imidazo[1,2-a]pyrimidine and chlorosulphonic acid) and 40% methylamine analogously to Example 25.

Yield: 59.8% of theory, M.p.: 205°–210° C. Calculated: C 43.59 H 4.14 N 13.55 S 7.76 Br 19.33: Found: 43.86 3.96 13.60 8.25 19.31.

EXAMPLE 41

2-(2Methoxy-4-dimethylaminosulphonyl-phenyl)-imidazo[1,2-a]pyrimidine

Prepared from 2-amino-pyrimidine and α-bromo-2-methoxy-4-dimethylaminosulphonyl-acetophenone analogously to Example 1.

Yield: 54.2% of theory, M.p.: 233°–236° C. Calculated: C 54.20 H 4.85 N 16.85 S 9.65: Found: 54.50 4.74 16.94 9.73.

EXAMPLE 42

2-(2-Methoxy-4-dimethylaminosulphonyl-phenyl)-imidazo[1,2-a]pyridine

Prepared from 2-amino-pyridine and α-bromo-2-methoxy-4-dimethylaminosulphonyl-acetophenone analogously to Example 1.

Yield: 65.1% of theory, M.p.: 223°–225° C. Calculated: C 57.99 H 5.17 N 12.68 S 9.67: Found: 57.75 5.02 12.46 9.67.

EXAMPLE 43

6-Chloro-2-(1-methoxy-naphth-2-yl)-imidazo[1,2-la]pyridine

Prepared from 2-Amino-5-chloro-pyridine and α-Bromo-2-(1-methoxy)-acetophenone analogously to Example 1.

Yield: 57% of theory, M.p.: 155°–156° C. Calculated: C 70.02 H 4.24 N 9.07: Found: 69.97 4.18 9.01.

EXAMPLE 44

7-(Naphth-2-yl)-imidazo[2,1-c][1,2,4]triazine

Prepared from α-bromo-2-acetonaphthone and 3-amino[1,2,4]triazine analogously to Example 1.

Yield: 20.0% of theory, M.p.: 215°–216° C. Calculated: C 73.16 H 4.09 N 22.75: Found: 72.98 4.15 22.48.

EXAMPLE 45

2-(1-Methoxy-naphth-4-yl)-imidazo[1,2-a]pyrimidine

Prepared from α-bromo-4-(1-methoxy)-acetonaphthone and 2-amino-pyrimidine analogously to Example 1.

Yield: 11% of theory, M.p.: 180°–189° C. Calculated: C 74.17 H 4.76 N 15.26: Found: 74.08 4.76 15.28.

EXAMPLE 46

2-(1-Methyl sulphonyloxy-naphth-4-yl)-imidazo[1,2-a]pyrimidine

Prepared from 2-(1-hydroxy-naphth-4-yl)-imidazo[1,2-a]pyrimidine and methanesulphonic acid chloride analogously to Example 2.

Yield: 26% of theory, M.p.: 199°–200° C. Calculated: C 60.16 H 3.86 N 12.38: Found: 60.01 3.81 12.41.

EXAMPLE 47

2-(1-Methoxy-naphth-2-yl)-imidazo[1,2-a]pyridine

Prepared from 6-Chloro-2-(1-methoxy-naphth-2-yl)-imidazo-[1,2-a]-pyridine analogously to Example 54.

Yield: 6% of theory, M.p.: 146°–148° C. Calculated: C 78.81 H 5.14 N 10.21: 78.93 5.23 10.23.

EXAMPLE 48

2-(2-Methoxy-naphth-6-yl)-imidazo[1,2-a]pyrimidine

Prepared from α-bromo-6-(2-methoxy)-acetonaphthone and 2-amino-pyrimidine analogously to Example 1.

Yield: 22% of theory, M.p.: 268°–269° C. Calculated: C 74.17 H 4.76 N 15.26: Found: 74.07 5.00 15.22.

EXAMPLE 49

2-(1-Hydroxy-naphth-4-yl)-imidazo[1,2-a]pyrimidine 1.38 g (5 mmol) of 2-(1-methoxy-naphth-4-yl)-imidazo[1,2-a]pyrimidine are suspended in 50 ml of methylene chloride, cooled to −40° C. and 1.15 ml (12 mmol) of boron tribromide are added dropwise with stirring. The mixture is then stirred for 14 hours at ambient temperature, 30 ml of ethanol are added and the mixture is stirred for a further 30 minutes. It is then concentrated to dryness in vacuo and the crude product thus obtained in purified by column chromatography.

Yield: 48% of theory, M.p.: 241°–242° C. Calculated: C 73.55 H 4.24 N 16.08: Found: 73.33 4.20 16.32.

EXAMPLE 50

2-(4-Amino-2-methoxy-phenyl)-imidazo[1,2-b]pyridazine 0.3 g (1 mmol) of 2-(4-Acetamino-2-methoxyphenyl)-imidazo[1,2-b]pyridazine are heated for 1½ hours in 20 ml of 6N hydrochloric acid over a steam bath. After cooling and filtration, the residue is made alkaline with conc. ammonia. The product precipitated is suction filtered, washed with water and dried at 100° C. over potassium hydroxide in a drying gun.

Yield: 71% of theory, M.p.: 197°–198° C. (decomposition) Calculated: C 64.99 H 5.03 N 23.32: Found: 65.30 5.00 23.56.

EXAMPLE 51

2-(4-Aminosulphonyl-2-methoxy-phenyl)-6-chloro-imidazo[1,2-b]pyridazine 0.6 g (4.5 mmol) of 3-Amino-6-chloro-pyridazine and 0.7 g (2.27 mmol) of α-bromo-4-aminosulphonyl-2-methoxy-acetophenone are dissolved in 10 ml of dimethylformamide, then stirred for 22 hours at ambient temperature and for 30 minutes at 50° C. Half the dimethylformamide is then removed using a water jet vacuum and the residue is poured onto 50 ml of ice water. The product precipitated is suction filtered, washed with water and dried in a drying gun at 100° C. over potassium hydroxide.

Yield: 83% of theory, M.p.: 310°–311° C. (decomp.) Calculated: C 46.09 H 3.27 N 16.54 Cl 10.47 S 9.47: Found: 45.98 3.31 16.68 10.72 9.56.

EXAMPLE 52

2-(4-Acetamino-2-methoxy-phenyl)-imidazo[1,2-b]pyridazine-hydrobromide 2 g (5 mmol) of 2-(4-Acetamino-5-bromo-2-methoxyphenyl)-6-chloro-imidazo[1,2-b]pyridazine are suspended in 100 ml of dimethylformamide, mixed with 0.28 g (5 mmol) of ground potassium hydroxide and hydrogenated for 50 minutes at ambient temperature and in a Parr apparatus with 0.5 g of 20% Pd/C under a hydrogen pressure of 5 bar. Then 25 ml of water are added and the catalyst is filtered off. The mother liquor is concentrated by centrifuging and after stirring with 50 ml of water it is suction filtered, washed with water and dried in a vacuum drying cupboard at 50° C. over phosphorus pentoxide.

Yield: 78% of theory, M.p.: 278°–285° C. (decomp.) Mass spectrum: M+ =282 m/e.

EXAMPLE 53

2-(4-Methylsulphonylamino-2-methoxy-phenyl)-imidazo[1,2-b]pyridazine

Prepared from 2-(4-amino-2-methoxy-phenyl)-imidazo[1,2-b]pyridazine and methanesulphonochloride in pyridine analogously to Example 2.

Yield: 82% of theory, M.p.: 231° C. Calculated: C 52.81 H 4.43 N 17.60 S 10.07: Found: 52.70 4.61 17.43 10.14.

EXAMPLE 54

2-(4-Dimethylaminosulphonyl-2-methoxy-phenyl)-6-chloro-imidazo[1,2-b]pyridazine

Prepared from 3-amino-6-chloro-pyridazine and α-bromo-4-dimethylaminosulphonyl-2-methoxy-acetophenone analogously to Example 1.

Yield: 72% of theory, M.p.: 214°–215° C. Calculated: C 49.11 H 4.12 N 15.27 Cl 9.67 S 8.74: Found: 49.35 4.15 15.24 9.89 8.47.

EXAMPLE 55

2-(4-Dimethylaminosulphonyl-2-methoxy-phenyl)-imidazo[1,2-b]pyridazine

Prepared from 3-amino-pyridazine and α-bromo-4-dimethylaminosulphonyl-2-methoxy-acetophenone analogously to Example 1.

Yield: 6% of theory, M.p.: 215° C. (decomp.) Mass spectrum: M+ =332 m/e.

EXAMPLE 56

2-(4-Methylsulphonylamino-2-methoxy-phenyl)-6-chloro-imidazo[1,2-b]pyridazine

Prepared from 3-amino-6-chloro-pyridazine and α-bromo-4-methylsulphonylamino-2-methoxy-acetophenone analogously to Example 1.

Yield: 86% of theory, M.p.: 253°–257° C. (decomp.) Calculated: C 47.66 H 3.71 N 15.88 Cl 10.05 S 9.09: Found: 47.88 3.67 15.97 10.25 9.27.

EXAMPLE 57

2-(4-Aminosulphonyl-2-methoxy-phenyl)-imidazo[1,2-b]pyridazine

Prepared from 2-(4-aminosulphonyl-2-methoxyphenyl)-6-chloro-imidazo[1,2-b]pyridazine and hydrogen in the presence of Pd/C analogously to Example 54.

Yield: 16% of theory, M.p.: 267°–277° C. (decomp.)
Mass spectrum: M+ = 304 m/e.

EXAMPLE 58

6-(2-Methoxy-4-methylsulphonyloxy-phenyl)-imidazo[2,1-f][1,2,4]triazine 55 mg (0.227 mmol) of 6-(2-Methoxy-4-hydroxyphenyl)-imidazo[2,1-f][1,2,4]triazine are dissolved in 12 ml of 1N sodium hydroxide solution. 0.2 ml of methanesulphonic acid chloride are added to the clear yellowish-orange solution and the resulting mixture is stirred for 2½ hours at ambient temperature. The reaction solution is then adjusted to pH 6 with 1N hydrochloric acid and extracted three times, each time with 25 ml of ethyl acetate. The ethyl acetate phase is dried over sodium sulphate and concentrated by evaporation. The residue obtained is dissolved in methylene chloride and applied to a silica gel column, eluting first with methylene chloride and later with methylene chloride/ethanol (50:1). The desired eluates are concentrated by evaporation, then triturated with ether/petroleum ether (1:1) and the crystals obtained are suction filtered.

Yield: 15 mg (20.7% of theory), M.p.: 202°–204° C. Mass spectrum: M+ = 320 m/e.

EXAMPLE 59

2-(2-Methoxy-4-methylaminocarbonyl-phenyl)-imidazo[1,2-a]pyridine

Prepared from 2-amino-pyridine and α-bromo-2-methoxy-4-methylaminocarbonyl-acetophenone analogously to Example 1.

Yield: 50% of theory, M.p.: 235°–237° C. Calculated: C 68.31 H 5.37 N 14.94: Found: 68.20 5.48 15.13.

EXAMPLE 60

2-(2-Methoxy-4-dimethylaminocarbonyl-phenyl)-imidazo[1,2-a]pyrimidine

Prepared from 2amino-pyrimidine and α-bromo-2-methoxy-4-dimethylaminocarbonyl-acetophenone analogously to Example 1.

Yield: 49.1% of theory, M.p.: 212°–214° C. Calculated: C 64.85 H 5.44 N 18.91: Found: 65.06 5.68 18.73.

The following compounds are obtained analogously to the preceding Examples:

2-(4-Aminosulphonyl-phenyl)-imidazo[1,2-a]pyridine
2-(4-Methylaminosulphonyl-phenyl)-imidazo[1,2-a]pyridine
2-(4-Aminocarbonyl-phenyl)-imidazo[1,2-a]pyridine
2-(4-Methylaminocarbonyl-phenyl)-imidazo[1,2-a]pyridine
2-(4-Dimethylaminocarbonyl-phenyl)-imidazo[1,2-a]pyridine
2-(4-Methoxy-3-dimethylaminosulphonyl-phenyl)-imidazo[1,2-a]pyrazine
2-(2,4-Dimethoxy-5-dimethylaminosulphonyl-phenyl)-imidazo[1,2-a]pyrazine
7-(4-Methoxy-3-dimethylaminosulphonyl-phenyl)-imidazo[2,1-c][1,2,4]triazine
7-(2,4-Dimethoxy-5-dimethylaminosulphonyl-phenyl)-imidazo[2,1-c][1,2,4]triazine
2-(4-Dimethylaminosulphonyl-2-methoxy-phenyl)-imidazo[1,2-c]pyrimidine
2-(2-Methoxy-4-aminosulphonyl-phenyl)-imidazo[1,2-c]pyrimidine
2-(2-Methoxy-4-methylaminosulphonyl-phenyl)-imidazo[1,2-c]pyrimidine
2-(4-Dimethylaminosulphonyl-phenyl)-imidazo[1,2-c]pyrimidine
2-(2-Methoxy-4-methylsulphonamido-phenyl)-imidazo[1,2-c]pyrimidine
2-(4-Methylsulphonyloxy-phenyl)-imidazo[1,2-c]pyrimidine
2-(2-Methoxy-4-methylsulphonyloxy-phenyl)-imidazo[1,2-c]pyrimidine
2-(2-Methoxy-4-aminosulphonyl-phenyl)-imidazo[1,2-b]pyridazine,
2-(4-Dimethylaminosulphonyl-2-methoxy-phenyl)-imidazo[1,2-b]pyridazine
6-Amino-2-(2-methoxy-4-methylsulphonamido-phenyl)-imidazo[1,2-b]pyridazine
6-Acetamido-2-(2-methoxy-4-methylsulphonamido-phenyl)-imidazo[1,2-b]pyridazine
6-Dimethylamino-2-(2-methoxy-4-methylsulphonamido-phenyl)-imidazo[1,2-b]pyridazine
2-(4-Benzyloxy-2-methoxy-phenyl)-6-chloro-imidazo[1,2-b]pyridazine
2-(4-Hydroxy-2-methoxy-phenyl)-imidazo[1,2-b]pyridazine
2-(2-Methoxy-4-methylsulphonyloxy-phenyl)-imidazo[1,2-b]pyridazine
2-(4-Methylsulphonamido-phenyl)-6-methylsulphonyloxy-imidazo[1,2-b]pyridazine
2-(4-Aminosulphonyl-phenyl)-imidazo[1,2-b]pyridazine
2-(4-Dimethylaminosulphonyl-phenyl)-imidazo[1,2-b]pyridazine
2-(4-Acetamido-phenyl)-6-chloro-imidazo[1,2-b]pyridazine
2,4-Bis(methylmercapto)-6-(4-benzyloxy-2-methoxy-phenyl)-imidazo[2,1-f][1,2,4]triazine
6-(4-Hydroxy-2-methoxy-phenyl)-imidazo[2,1-f][1,2,4]triazine
6-(2-Methoxy-4-methylsulphonyloxy-phenyl)-imidazo[2,1-f][1,2,4]triazine
2-(2-Methoxy-4-methylsulphonyloxy-phenyl)-imidazo[1,2-d][1,2,4]triazine
2-(2-Methoxy-4-methylsulphonylamido-phenyl)-imidazo[1,2-d][1,2,4]triazine
2-(4-Methylsulphonyloxy-phenyl)-imidazo[1,2-d][1,2,4]triazine
2-(2-Methoxy-4-aminosulphonyl-phenyl)-imidazo[1,2-d][1,2,4]triazine
2-(2-Methoxy-4-methylaminosulphonyl-phenyl)-imidazo[1,2-d][1,2,4]triazine
2-(2-Methoxy-4-dimethylaminosulphonyl-phenyl)-imidazo[1,2-d][1,2,4]triazine

EXAMPLE A

Tablets containing 100 mg of
2-(2-methoxy-4-methylsulphonyloxyphenyl)-imidazo-[1,2-a]pyrazine

| Composition 1 tablet contains: | |
|---|---|
| Active substance | 100.0 mg |
| Lactose | 50.0 mg |

-continued

| Composition 1 tablet contains: | |
|---|---|
| Polyvinylpyrrolidone | 5.0 mg |
| Carboxymethylcellulose | 19.0 mg |
| Magnesium stearate | 1.0 mg |
| | 175.0 mg |

Moist screening: 1.5 mm
Drying: circulating air dryer 50° C.
Dry screening: 1 mm
The remaining excipients are added to the granules and the final mixture is compressed to form tablets.
Weight of tablet: 175 mg
Punch: 8 mm

EXAMPLE B

Coated tablets containing 50 mg of 2-(2-methoxy-4-methyl-sulphonyloxyphenyl)-imidazo-[1,2-a]pyrazine

| Composition: 1 tablet core contains: | |
|---|---|
| Active substance | 50.0 mg |
| Dried corn starch | 20.0 mg |
| Soluble starch | 2.0 mg |
| Carboxymethylcellulose | 7.0 mg |
| Magnesium stearate | 1.0 mg |
| | 80.0 mg |

The active substance and starch are homogeneously moistened with an aqueous solution of the soluble starch.
Moist screening: 1.0 mm
Dry screening: 1.0 mm
Drying: 50° C. in a circulating air dryer The granulate and other excipients are mixed together and compressed to form tablet cores.
Weight of core: 80 mg
Punch: 6 mm
Radius of curvature: 5 mm
The finished cores are provided with a sugar coating in a coating pan in the usual way. Weight of coated tablet: 120 mg

EXAMPLE C

Suppositories containing 75 mg of 2-(2-methoxy-4-methylsulphonyloxyphenyl)-imidazo-[1,2-a]pyrazine

| 1 suppository contains: | |
|---|---|
| Active substance | 75.0 mg |
| Suppository mass (e.g. Witepsol H 19 and Witepsol W 45) | 1625.0 mg |
| | 1700.0 mg |

Method of preparation:
The suppository mass is melted. At 38° C. the ground active substance is homogeneously dispersed in the melt. It is cooled to 35° C. and poured into chilled suppository moulds. Weight of suppository: 1.7 g

EXAMPLE D

Ampoules containing 50 mg of 2-(2-methoxy-4-methylsulphonyloxyphenyl)-imidazo-[1,2-a]pyrazine

| 1 ampoule contains: | |
|---|---|
| Active substance | 50.0 mg |
| Ethoxylated hydroxystearic acid | 250.0 mg |
| 1,2-Propylene glycol | 1000.0 mg |
| Distilled water ad | 5.0 ml |

Method of preparation
The active substance is dissolved in 1,2-propylene glycol and ethoxylated hydroxystearic acid, then made up to the specified volume with water and filtered sterile.
Bottling: in 5 ml ampoules
Sterilization: 20 minutes at 120° C.

EXAMPLE E cl Drops containing 100 mg of 2-(2-methoxy-4-methylsulphonyloxyphenyl)-imidazo-[1,2-a]pyrazine

| | |
|---|---|
| Active substance | 1.0 g |
| Methyl p-hydroxybenzoate | 0.035 g |
| Propyl p-hydroxybenzoate | 0.015 g |
| Anisole | 0.05 g |
| Menthol | 0.06 g |
| Sodium saccharin | 1.0 g |
| Glycerol | 10.0 g |
| Ethanol | 40.0 g |
| Distilled water ad | 100.0 ml |

Method of preparation
The benzoates are dissolved in ethanol and then the anisole and menthol are added. The active substance, glycerol and sodium saccharin dissolved in water are then added. The solution is filtered clear.

What is claimed is:
1. An imidazo[1,2-a]pyridine of the formula

$$\text{(I)}$$

wherein
one of the groups A, B, C or D is a —CH= group optionally substituted by a halogen atom or by an alkylmercapto, alkylsulphonyloxy, amino, alkylamino, dialkylamino or acetamido group;
another of the groups A, B, C or D is a —CH= group optionally substituted by an alkylmercapto group; and,
the other groups A, B, C or D are —CH= groups;
$R_1$ and $R_2$ together with two carbon atoms of the phenyl ring between them form a phenyl ring optionally substituted by an alkoxy group; and, when $R_1$ and $R_2$ do form such a phenyl ring,
$R_3$ is a hydrogen atom, a hydroxy, alkoxy or alkylsulphonyloxy group; or,
$R_1$ a phenylalkoxy, alkylsulphonyloxy, alkylsulphonamido, N-alkyl-alkylsulphonamido, aminosulphonyl, alkylaminosulphonyl or dialkylaminosulphonyl group or in the 4 position an acetamido, aminocarbonyl, alkylaminocarbonyl or dialkylaminocarbonyl group, it being provided that if one or two of the groups A, B, C or D are one of the above-mentioned substituted —CH= groups, then $R_1$ may also represent an amino, hydroxy, methoxy or cyano group in the 4 position;

$R_2$ is a hydrogen atom, a hydroxy or alkoxy group; and, $R_3$ is a hydrogen atom or an alkoxy group;

wherein in all the above-mentioned groups the alkyl part may contain one or two carbon atoms;

or, a pharmaceutically acceptable acid addition salt thereof.

2. An imidazo[1,2-a]pyridine of formula I, as claimed in claim 1, wherein one of the group A, B, C or D is a —CH= group optionally substituted by a chlorine or bromine atom or by a methylmercapto, methylsulphonyloxy, amino, methylamino, dimethylamino or acetamido group;

another of the groups A, B, C or D is a —CH= group optionally substituted by a methylmercapto group; and, the other group, A, B, C or D are —CH= groups;

$R_1$ and $R_2$ together with two carbon atoms of the phenyl ring between them form a phenyl ring optionally substituted by a methoxy group and, when $R_1$ and $R_2$ form such a phenyl ring, $R_3$ represents a hydrogen atom, a hydroxy, methoxy or methanesulphonyloxy group; or, $R_1$ is a methylsulphonyloxy, methylsulphonamido, N-methyl-methyl-sulphonamido, aminosulphonyl, methylaminosulphonyl or dimethylaminosuphonyl or in the 4-position an acetamido, aminocarbonyl, methylaminocarbonyl or dimethylaminocarbonyl group;

$R_2$ is a hydrogen atom or a hydroxy or methoxy group; and $R_3$ is a hydrogen or a methoxy group.

3. An imidazo[1,2-a]pyridine of formula I, as claimed in claim 1, wherein the groups A, B, C and D are —CH= groups.

4. An imidazo[1,2-a]pyridine of formula I, as claimed in claim 3, wherein $R_1$ is in the 2 or 4 position and $R_2$ is in the remaining 2 or 4 position.

5. An imidazo[1,2-a]pyridine of formula I, as claimed in claim 3, wherein $R_1$ is in the 2 or 4 position and is a methylsulphonyloxy, methylsulphonamido, N-methylmethylsulphonamido, aminosulphonyl, methylaminosulphonyl or dimethylaminosulphonyl group;

$R_2$ is in the remaining 2 or 4 position and is a methoxy group; and, $R_3$ is a hydrogen atom.

6. 2-(2-methoxy-4-methylsulphon-amidophenyl)-imidazo[1,2-a]pyridine or a pharmaceutically acceptable acid addition salt thereof.

7. A pharmaceutical composition for treating heart failure characterized by reduced cardiac output containing an effective positive inotropic amount of a compound of claim 1 together with a pharmaceutically acceptable carrier.

8. A method of treating heart failure characterized by reduced cardiac output which comprises administering to a host suffering from same an effective positive inotropic amount of a compound of claim 1, 2, 3, 4, 5 or 6.

* * * * *